United States Patent

Ochs et al.

[11] Patent Number: 5,944,741
[45] Date of Patent: Aug. 31, 1999

[54] ENVIRONMENT-RESPONSIVE METHOD FOR MAINTAINING AN ELECTRONIC DEVICE

[75] Inventors: Dennis E. Ochs, Bellevue; Ian G. MacDuff, Bothell; Daniel J. Powers, Issaquah, all of Wash.

[73] Assignee: Heartstream, Inc., Seattle, Wash.

[21] Appl. No.: 09/021,678

[22] Filed: Feb. 10, 1998

Related U.S. Application Data

[62] Division of application No. 08/911,710, Aug. 15, 1997.

[51] Int. Cl.$^6$ ........................................... A61N 1/39
[52] U.S. Cl. .............................................. 607/5
[58] Field of Search .................... 607/1, 2, 4, 5, 607/6, 9, 27, 29, 63

[56] References Cited

U.S. PATENT DOCUMENTS

| | | |
|---|---|---|
| 3,895,284 | 7/1975 | Schweizer et al. . |
| 4,207,514 | 6/1980 | Klein . |
| 4,323,849 | 4/1982 | Smith . |
| 4,525,055 | 6/1985 | Yokoo . |
| 4,693,119 | 9/1987 | Johnson . |
| 4,725,784 | 2/1988 | Peled et al. . |
| 4,931,737 | 6/1990 | Hishiki . |
| 5,065,084 | 11/1991 | Oogita . |
| 5,130,659 | 7/1992 | Sloan . |
| 5,162,741 | 11/1992 | Bates . |
| 5,440,221 | 8/1995 | Landau et al. . |
| 5,454,710 | 10/1995 | Landau et al. . |
| 5,483,165 | 1/1996 | Cameron et al. . |
| 5,800,460 | 9/1998 | Powers et al. ................ 607/5 |

FOREIGN PATENT DOCUMENTS

WO 94/27674   12/1994   WIPO .

*Primary Examiner*—William E. Kamm
*Assistant Examiner*—George R. Evanisko
*Attorney, Agent, or Firm*—Cecily Anne Snyder

[57] ABSTRACT

A method of indicating operational status of an electronic device, the device providing an indication of device operational status as a result of a self-test, the method including the following steps: monitoring an environmental condition; changing an indication of device operational status from a first indication to a second indication if the monitored environmental condition changes from a first condition to a second condition, this changing step being performed without performing a self-test. In certain embodiments, the monitored environmental condition is a monitored temperature, the first condition is a first temperature and the second condition is a second temperature. The electronic device may be battery-operated, in which case the self-test is a battery capacity test. In these embodiments, the method also may include the step of performing the battery capacity test when the monitored temperature reaches the second temperature if there is no indication of device operational status corresponding to the second temperature stored in memory, the second temperature is lower than a temperature associated with an indication of a non-waning device operational status stored in memory, and the second temperature is higher than a temperature associated with an indication of a warning operational status; and indicating device operational status as a result of the battery capacity test. The method may also include the step of storing in memory an association between the second temperature and device operational status.

14 Claims, 5 Drawing Sheets

5,944,741

ENVIRONMENT-RESPONSIVE METHOD FOR MAINTAINING AN ELECTRONIC DEVICE

RELATED APPLICATION

This application is a divisional of application Ser. No. 08/911,710 filed Aug. 15, 1997.

BACKGROUND OF THE INVENTION

1. Field of the Invention

This invention relates generally to electronic devices and environment-dependent methods of maintaining the devices and indicating operational status of the devices. In particular, this invention relates to temperature-dependent methods of maintaining battery-operated external defibrillators and indicating their operational status.

2. Description of the Prior Art

Electronic devices that are infrequently used may be designed to perform automatic self-tests on a preset schedule, in response to an event or condition, or otherwise and to indicate the results of those self-tests to a potential user. An example can be found in certain external defibrillators that automatically self-test battery capacity and other defibrillator functions and components and indicate the results of those self-tests (i.e., the device's operational status) through visual displays and/or audible tones.

U.S. patent application Ser. No. 08/240,272 describes a battery-operated automatic external defibrillator (AED) designed for infrequent use. The device described in that patent application performs a variety of daily, weekly and monthly self-tests while in stand-by mode (i.e., when not powered-on to treat a patient, to review past treatment events, etc.) and indicates the operational status of the device using an "OK" or "Not OK" fail-safe visual display and using an audible tone generator. One of the device parameters monitored during the self-tests is remaining battery capacity.

The '272 application also suggests performing a group of self-tests automatically in response to exposure of the defibrillator to temperature extremes, although the exact nature of the environmentally-triggered self-tests is not disclosed. The disclosure of the '272 application is incorporated herein by reference.

There are many other types of battery-operated devices as well. Some battery-operated devices automatically track remaining battery capacity and indicate device status or make some other change based, at least in part, on remaining battery capacity. See, e.g., U.S. Pat. No. 3,895,284; U.S. Pat. No. 4,207,514; U.S. Pat. No. 4,525,055; U.S. Pat. No. 4,693,119; U.S. Pat. No. 4,725,784; U.S. Pat. No. 4,931,737; U.S. Pat. No. 5,065,084; U.S. Pat. No. 5,130,659; U.S. Pat. No. 5,162,741; and U.S. Pat. No. 5,483,165. The disclosures of these patents are incorporated herein by reference.

For example, Bates U.S. Pat. No. 5,162,741 describes a battery monitor that continuously samples the battery load current and temperature. The device continuously displays remaining battery capacity based on a temperature-compensated measurement of the amount of current drawn from the battery.

Hishiki U.S. Pat. No. 4,931,737 describes a battery capacity measurement circuit using a capacitor having thermal and age-variation characteristics to compensate for the thermal and age-variation characteristics of the battery. Specifically, the capacitor's capacitance, like the battery capacity, is maximum at room temperature and decreases with either an increase or decrease in ambient temperature. The capacitor is used to generate a pulse signal whose frequency varies with temperature as the capacitance (and therefore the battery capacity) changes, with the frequency being lowest at room temperature and increasing with an increase or decrease in ambient temperature. The pulse signals are counted by a counter to compute battery discharge and, thereby, remaining battery capacity.

Landau et al. U.S. Pat. No. 5,454,710 describes a battery monitoring and display system which adjusts actual measurements of remaining battery capacity by fixed percentages when the ambient temperature is in certain defined ranges.

SUMMARY OF THE INVENTION

An indication of device operating status can be critically important for certain electronic devices. For example, external defibrillators are used to treat victims of sudden cardiac arrest through the delivery of an electric shock. Time is of the essence in getting this defibrillation therapy to the victim. In fact, the patient's chances of survival are reduced by about 10% for each minute that therapy is withheld. If a defibrillator incorrectly reports its operational status, valuable time can be lost in determining the cause of the error and remedying the problem. A defibrillator's operational status indicator must therefore be extremely reliable in its indication of device status.

Environmental conditions can materially affect the operational status of an electronic device (such as a defibrillator). In particular, high and, especially, low temperatures can have a dramatic affect on available battery capacity. It is therefore an object of this invention to take ambient environmental conditions into account when indicating operational status of an electronic device, making that status indication more responsive to environmental changes, and thereby improving the reliability of that status indication.

Self-testing itself can materially affect the operational status of an electronic device by, for instance, depleting resources such as battery power. It is therefore another object of this invention to change, under certain environmental conditions, the indication of device operational status based on historical self-test results without actually performing a new self-test.

The invention is a method of indicating operational status of an electronic device (such as an external defibrillator), the device providing an indication of device operational status as a result of a self-test, the method including the following steps: monitoring an environmental condition (such as temperature); changing an indication of device operational status from a first indication to a second indication if the monitored environmental condition changes from a first condition to a second condition, this changing step being performed without performing a self-test. The first indication may be a non-warning indication and the second indication may be a warning indication. In one embodiment, the second condition is a target condition, and the method further includes the step of setting a new target condition.

In certain embodiments, the monitored environmental condition is a monitored temperature, the first condition is a first temperature and the second condition is a second temperature. The electronic device may be battery-operated, in which case the self-test is a battery capacity test. In these embodiments, the method also may include the step of performing the battery capacity test when the monitored temperature reaches the second temperature if there is no indication of device operational status corresponding to the second temperature stored in memory, the second temperature is lower than a temperature associated with an indication of a non-warning device operational status stored in memory, and the second temperature is higher than a temperature associated with an indication of a warning operational status; and indicating device operational status as a result of the battery capacity test. The method may also include the step of storing in memory an association between the second temperature and device operational status.

In other embodiments, the method includes, without performing a self-test, the step of changing the indication of device operational status from the second indication to the first indication if the monitored environmental condition reaches the first condition. The method may also include the step of retrieving from memory the second indication of device operational status, the second indication of device operational status being associated with the second condition. In such case, the method may include, following the retrieving step but prior to the changing step, the step of determining whether the second indication of device operational status is valid, the changing step being performed only if the second indication of device operational status is valid. The method may also include the step of performing a self-test if the second indication of device operational status is invalid.

In still other embodiments, the method includes the steps of performing an automatic self-test when the monitored environmental condition reaches the second condition if there is no indication of device operational status corresponding to the second condition stored in memory; and indicating device operational status as a result of the self-test. The method may also include storing in memory an association between the second condition and device operational status.

In another embodiment, the invention is a method of indicating operational status of a battery-operated, automatically self-testing device (such as an external defibrillator), the device providing an indication of device operational status as a result of a self-test, and includes the following steps: monitoring a temperature; if the monitored temperature reaches a target temperature, retrieving from memory associations between temperature and indications of device operational status; if the highest temperature associated with an indication of a warning device operational status is higher than the lowest temperature associated with an indication of a non-warning device operational status, performing an automatic battery capacity test and indicating device operational status as a result of the battery capacity test. In one embodiment, the method includes the step of storing in memory an association between the target temperature and an indication of device operational status.

In yet another embodiment, the invention is a method of indicating operational status of an electronic device (such as an external defibrillator), including the following steps: monitoring an environmental condition (such as temperature); performing a plurality of self-tests (such as battery capacity tests) at a plurality of environmental conditions to determine as self-test results whether device operational status is acceptable or unacceptable at each environmental condition; storing an association of self-test results and environmental conditions at which the self-tests were performed; and indicating operational status of the electronic device based on the self-test results. In one embodiment, the method includes the step of storing a maximum number of self-test results.

In one particular embodiment the environmental condition is temperature and the self-test is a battery-capacity test, and the method includes the following steps: if a battery capacity test has not been performed at a target temperature, and if the target temperature is lower than the temperature of the lowest acceptable battery capacity test result and higher than the temperature of the highest unacceptable battery capacity test result: performing a battery capacity test;

storing an association of a battery capacity test result from the previous step and the target temperature; indicating the battery capacity test result stored in the previous step; and setting a new target temperature.

The method may also include, if a temperature of an unacceptable battery capacity test result is higher than a temperature of an acceptable battery capacity test result, the steps of:

performing a battery capacity test; storing an association of a battery capacity test result from the previous step and temperature; and indicating the battery capacity test result stored in the previous step. In this embodiment, the method may also include, if the device battery capacity has been tested at the target temperature, the step of indicating the stored battery capacity test result associated with the target temperature.

The invention will be described in more detail below with reference to the drawings.

DETAILED DESCRIPTION OF THE PREFERRED EMBODIMENTS

As discussed above, environmental changes can affect the results of a battery self-test and potentially other self-tests as well. It is not always necessary, and sometimes undesirable, to run a self-test, however. One aspect of this invention, therefore, is a method of indicating the operational status (e.g., through a "warning" indication) of an electronic, self-testing device based on recent historical self-test results, without actually performing a new self-test, such as a battery capacity test. This aspect of the invention is illustrated with reference to the battery-operated external defibrillator shown in FIG. 1. It should be understood that this aspect of the invention is applicable to other battery-operated and non-battery-operated electronic devices as well.

Figure 1:
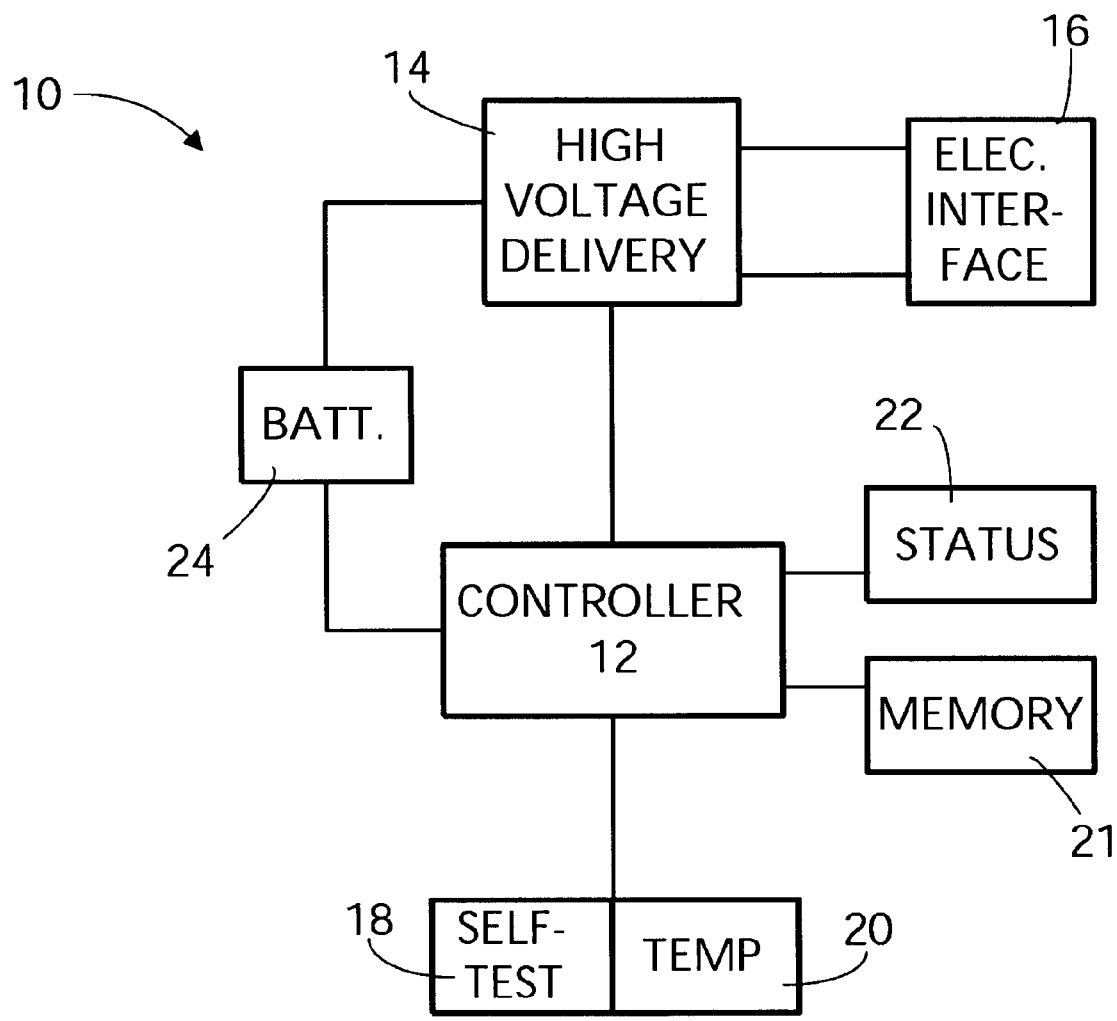
FIG. 1 is an example of a defibrillator which can be used to implement the methods of this invention.

In FIG. 1, external defibrillator 10 includes a high voltage delivery system 14 operating under the control of controller 12 to deliver an electric shock to an electrode interface 16. The high voltage delivery system may include a power transformer, switches and other circuit elements known in the defibrillator art. Power for operating the defibrillator and for the electrical shock comes from battery 24.

In the preferred embodiment, defibrillator 10 automatically performs self-tests under the control of a self-test system 18 and indicates its operational status on a status indicator 22. The self-tests may include a battery capacity test and tests of other defibrillator systems or components. Status indicator 22 may be any object which informs the user of device status through visual, audible, tactile, or other sensory means (e.g., a light, a text display, an electrically or mechanically altered symbol, a beeper, or a spoken word generator). The self-test system may be an integral part of the controller 12, of course, without departing from the scope of this invention.

Details of a defibrillator self-test system (including a battery capacity test) may be found in U.S. patent application Ser. No. 08/240,272, the disclosure of which is incorporated herein by reference. Details of a preferred battery capacity test may be found in U.S. Pat. No. 5,483,165, which is also incorporated herein by reference. The exact nature and design of the battery capacity test and other self-tests form no part of this invention.

Defibrillator 10 has a environmental sensor 20 which can be used to determine whether an environmental condition (such as temperature, humidity, chemical concentration, radiation level, altitude, mechanical shock or vibrations, etc.) is within the defibrillator's specified operating range and whether that environmental condition has exceeded some predefined limit. Controller 12 may also use sensor 20 to identify warning states or other device operational status and to indicate device status on status indicator 22 in response to a change in the environmental condition (whether or not the defibrillator is within its specified operating range) without performing a battery capacity test or other self-test.

External defibrillator 10 has at least three operational modes. In use mode, a controller 12 operates a high-voltage delivery system 14 to deliver an electrical shock to a patient through an electrode interface 16. In self-test mode, controller 12 automatically tests one or more of the defibrillator's circuits or functions (such as the defibrillator's battery) in response, for example, to a request for a self-test from a self-test initialization generator 18 and/or an environmental sensor 20 and indicates defibrillator operating status on a status indicator 22. More details about automatic self-tests in external defibrillators may be found in the '272 patent application. The exact nature of the self-tests is not a part of this invention, except as indicated herein.

Finally, in stand-by mode, controller 12 conserves power by simply monitoring temperature and other self-test initialization criteria (such as elapsed or real time) and by watching for a request to use the defibrillator, in which cases the defibrillator will move out of stand-by mode to self-test mode or use mode, respectively. Power for the electric shock and for operating the defibrillator is supplied by battery 24.

In one embodiment of the invention, defibrillator 10 stores in memory 21 associations between environmental conditions and device operational status indications. For example, warning indications may be stored in association with particular temperatures or temperature ranges, and non-warning indications may be stored in association with other temperatures or temperature ranges. In some cases, defibrillator 10 uses these stored associations between environmental conditions and device status indications to indicate warnings, or to remove warning indications, in response to environmental changes monitored by sensor 20 without actually performing new battery capacity tests or other self-tests.

Figure 2:
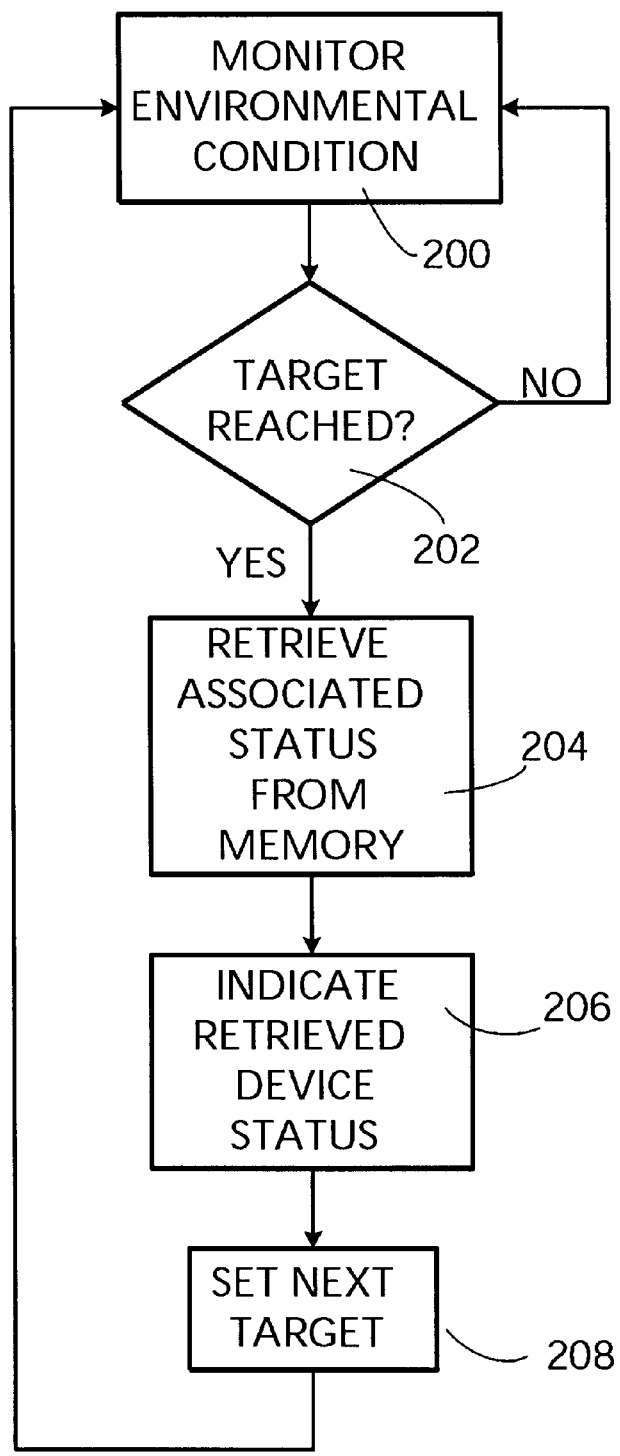
FIG. 2 is a flowchart showing one preferred method of indicating the operational status of a battery-operated, automatically self-testing device.

One preferred method of indicating the operational status of an electronic, self-testing device is shown in the flowchart of FIG. 2. An environmental condition (such as temperature, humidity, etc.) is monitored (block 200) to determine whether a predetermined target has been reached (block 202). If so, the device retrieves from memory any device operational status that may be stored in association with the target (block 204). At block 206, the device uses the stored status information to indicate device status on a device status indicator (such as status indicator 22 of the defibrillator shown in FIG. 1). At block 208, the device sets the next target that will trigger the retrieval of device status information from memory and continues to monitor the environmental condition. In this way, the device is able to indicate changes in device operational status based on historical self-test results without actually performing a new battery capacity test or other self-test.

Figure 3:
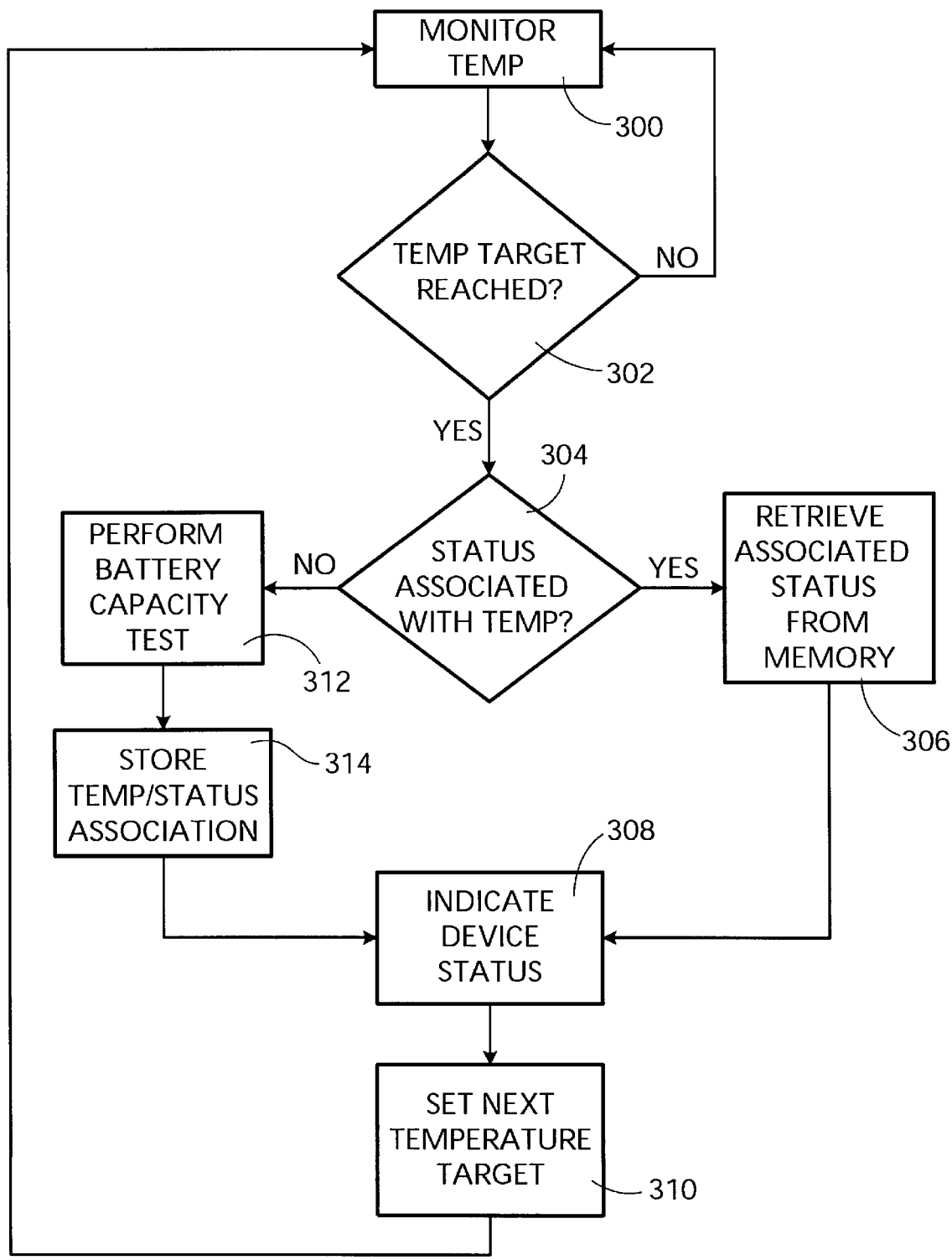
FIG. 3 is a flowchart showing another embodiment of the methods of this invention.

FIG. 3 is a flowchart showing another embodiment of the invention. In this embodiment, the environmental condition is temperature, which is monitored (block 300) to determine whether a predetermined temperature target has been reached (block 302). If there is a device operational status stored in device memory in association with the target temperature, the associated device operational status is retrieved from memory (block 306) and indicated via the device status indicator (block 308). If, however, there is no device operational status information stored in association with the target temperature, the device performs a battery capacity test or other self-test (block 312), stores in device memory an indication of device status in association with the target temperature (block 314) and indicates the newly-determined device status (block 308). A new temperature target is then set (block 310), and the device continues to monitor temperature.

Figure 4:
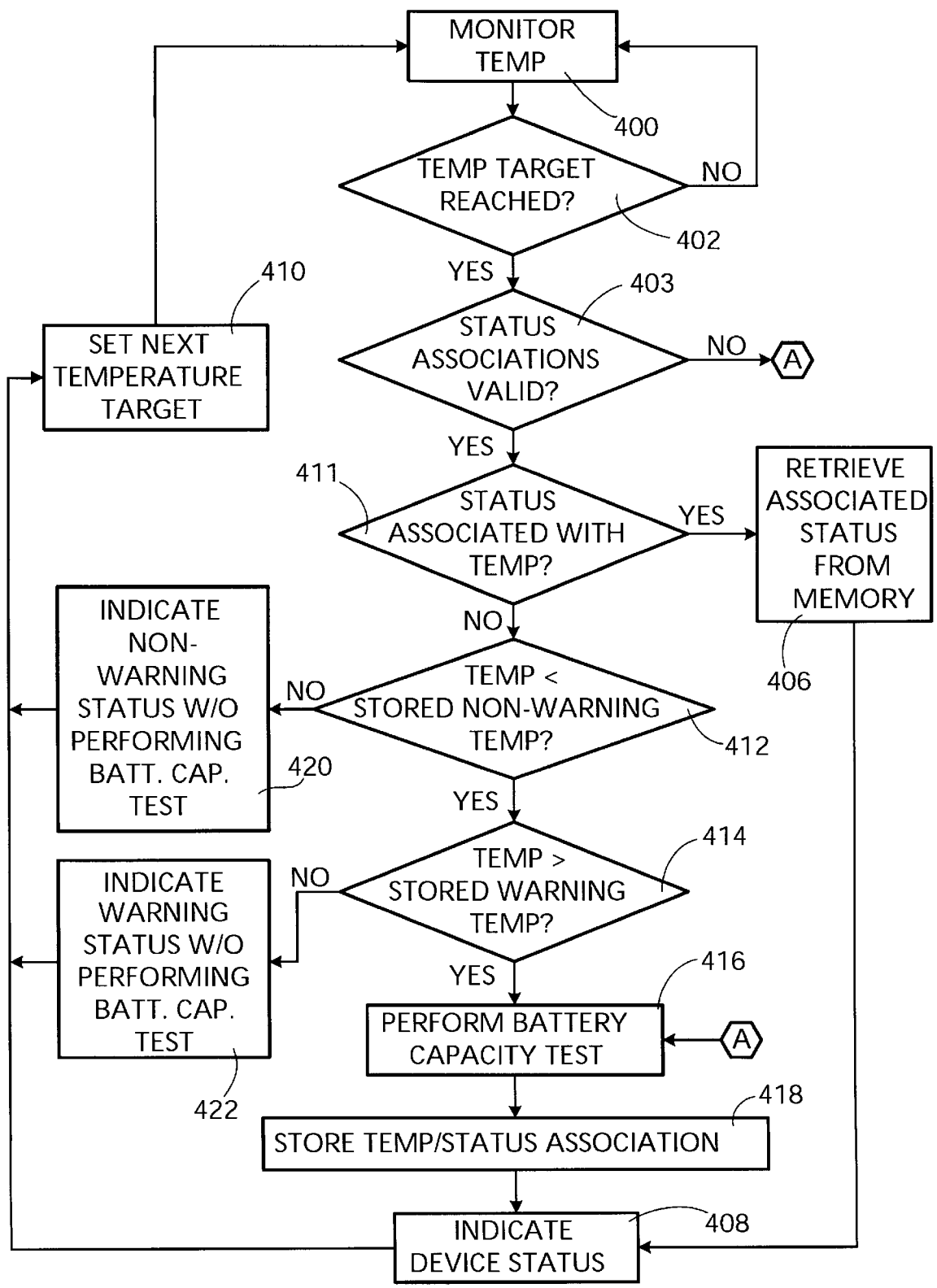
FIG. 4 is a flowchart showing yet another embodiment of this invention.

FIG. 4 is a flowchart showing yet another embodiment of this invention. This embodiment is based on the assumption that available battery capacity always decreases with a decline in temperature. As in the flowchart of FIG. 3, the device monitors temperature (block 400) and looks to see whether a temperature target has been reached (block 402). If so, the device determines whether there are valid temperature/status associations stored in memory (block 403). Stored associations may be invalid for many reasons, including age of the stored associations, recent use history of the device, etc. In a preferred embodiment, the device determines the validity of stored associations by determining whether the highest temperature stored in association with an indication of a warning device operational status is higher than the lowest temperature stored in association with an indication of a non-warning device operational status. The age of the stored associations are kept within 14 days by using only the last 14 associations stored, since the self-tests on which the associations are based are performed at a frequency no greater than once per day and since any postponement of a self-test invalidates the stored associations.

If the associations are valid, the device retrieves the associated device status from memory (block 406), indicates that status on the device status indicator (block 408), and sets the next temperature target (block 410). If, on the other hand, the stored temperature/status associations are not valid, the device ignores the stored temperature/status association and performs a battery capacity test (block 416) before indicating device status (block 408) and setting the next temperature target.

If there is no device operational status information stored in association with the target temperature, the device determines whether the target temperature is less than the lowest temperature stored in association with a non-warning (i.e., acceptable) device operational status (block 412). If not (i.e., if the target temperature is higher than a known non-warning temperature), based on the assumption that battery capacity increases with increasing temperature, the device indicates a non-warning status without performing a battery capacity test (block 420).

If the target temperature is less than the lowest temperature stored in association with a non-warning status but not greater than the highest temperature stored in association with a warning (i.e., unacceptable) device operational status (i.e., if the target temperature is cooler than a known warning temperature), the device indicates a warning status without performing a battery capacity test (block 422) based on the assumption that battery capacity decreases with a decrease in temperature.

It should be understood that, for purposes of this invention, the target temperatures may be temperature regions and not precise temperatures.

The following is a specific example of the methods of this invention as implemented in an external defibrillator such as defibrillator 10 in FIG. 1. In this example, the specified operating range for defibrillator 10 is 0° C. to 50° C. with the measurement accuracy being ±2.5° C. Defibrillator 10 maintains in device memory 21 a Recent Temperature History List (RTHL) containing the temperature reading and battery test results (e.g., "good battery" or "not good battery"; "warning" or "no warning"; etc.) for up to the most recent 14 battery capacity tests. The potential temperature measurements over the defibrillator's operating range are divided into bins as follows:

| Temperature Range | Classification Bin # |
|---|---|
| >52.5 C. | 8 |
| [30.0 to 52.5] C. | 7 |
| [20.0 to 30.0) C. | 6 |
| [12.5 to 20.0) C. | 5 |
| [7.5 to 12.5) C. | 4 |
| [2.5 to 7.5) C. | 3 |
| [−2.5 to 2.5) C. | 2 |
| [−7.5 to −2.5) C. | 1 |
| <−7.5 C. | 0 |

Temperature/status associations in the RTHL are invalidated whenever the defibrillator is actually used (i.e., when the device is placed in "use" mode) or when a battery is installed into the device since these actions can significantly alter the remaining battery capacity.

The algorithm assumes that the battery capacity always decreases with lower temperature and always increases or stays the same with higher temperature. In this example, defibrillator 10 is in a stand-by or power-down mode when it is not being used to treat a patient and is not running an automatic self-test. While in standby mode, defibrillator 10 checks temperature via its temperature sensor 20 every two seconds. When the defibrillator wakes up due to a temperature measurement at the high or low ends of its specified temperature range, the device will return to stand-by mode without any further tests. At the low end, the defibrillator will change the status indicator to indicate that the device is not ready to use.

If the present temperature is within the range of 0° C. to 50° C., the defibrillator extracts only the most recent valid battery capacity test result for each bin from the RTHL. If the present temperature bin (i.e., the bin encompassing the present ambient temperature) has not been tested and it is lower than the lowest passing bin and higher than the highest failing bin, the defibrillator runs its battery capacity test. Also, if the highest failing bin is higher than the lowest passing bin, the defibrillator runs its battery capacity test. Otherwise, the defibrillator sets the present battery capacity to reflect the previous test results from the RTHL without performing a battery capacity test: if the present bin is higher than a passing bin, the device indicates a "good battery" or non-warning status on its status indicator 22, and if the present bin is lower than a failing bin, the device indicates a "not good battery" or warning status on its status indicator 22.

In the preferred embodiment, the device sets both high and low target (or "wake-up") temperatures before returning to stand-by mode after a use, a self-test, etc. The following table illustrates how the HI and LO registers may be set:

| Temp Target Registers | No Low Battery | Low Battery |
|---|---|---|
| Instrument Temp in Bin 8 | HI = Bin 8 (disabled)<br>LO = Bin 7 | HI = Bin 8 (disabled)<br>LO = Bin 7 |
| Instrument Temp in Bins 2–7 | if highest fail bin < lowest pass bin:<br>HI = Bin 8 (disabled)<br>LO = MAX(1 Bin lower than lowest pass, Bin 1)<br>else:<br>HI = 1 Bin higher than present<br>LO = 1 Bin lower than present | if highest fail bin < lowest pass bin:<br>HI = 1 Bin higher than highest fail<br>LO = Bin 0 (disabled)<br>else:<br>HI = 1 Bin higher than present<br>LO = Bin 0 (disabled) |
| Instrument Temp in Bin 1 | HI = Bin 2<br>LO = Bin 0 (disabled) | if no postponed tests and highest fail bin < lowest pass bin:<br>HI = 1 Bin higher than highest fail<br>LO = Bin 0 (disabled)<br>else<br>HI = Bin 2<br>LO = Bin 0 (disabled) |
| Instrument Temp in Bin 0 | HI = Bin 1<br>LO = Bin 0 (disabled) | HI = Bin 1<br>LO = 0 (disable) |

| Target Bin # | Target Temperature |
|---|---|
| 8 | 70 C. (disabled) |
| 7 | 56 C. |
| 6 | 25 C. |
| 5 | 15 C. |
| 4 | 10 C. |
| 3 | 5 C. |
| 2 | 0 C. |
| 1 | −5 C. |
| 0 | −55 C. (disabled) |

Figure 5:
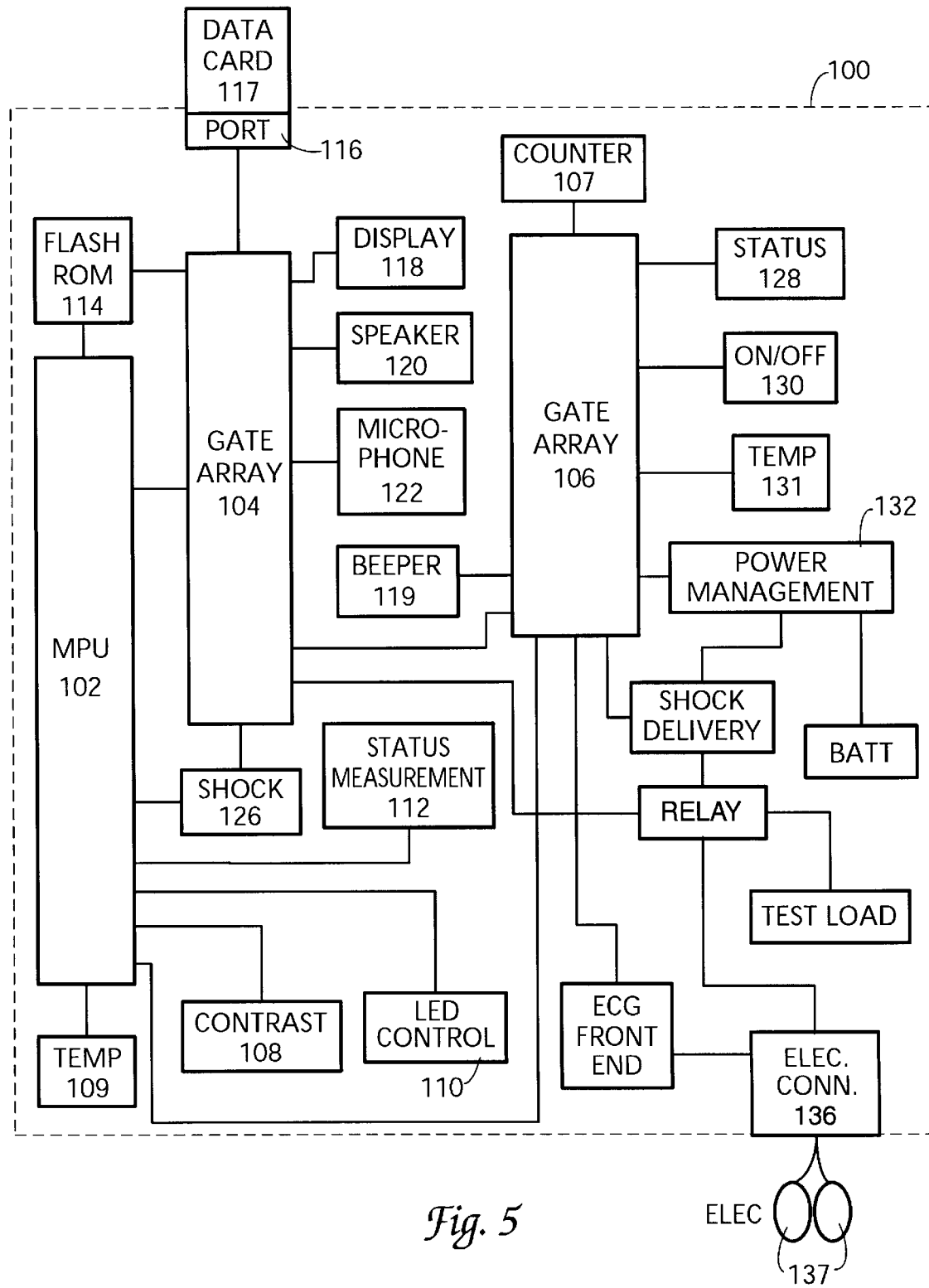
FIG. 5 is a block diagram showing an external defibrillator that may be used to implement the methods of this invention.

FIG. 5 is a block diagram showing an external defibrillator that may be used to implement the methods invention. Many of the elements shown in FIG. 5 bear no relation to this invention. They have been included solely to show one context in which the invention may operate.

As mentioned above, while defibrillators are particularly appropriate for implementing this invention, the invention is not limited to use in defibrillators. In the defibrillator shown in FIG. 5, battery capacity tests are run daily as part of a suite of automatic self-tests, and the results are recorded in the RTHL. The timing of the tests may be such, however, that hour-to-hour ambient temperature fluctuations are missed.

This invention therefore provides a way to take current temperature into account when providing a constant indication of device operational status.

In defibrillator 100 of FIG. 5, the functions of the controller of the FIG. 1 defibrillator are distributed among an MPU 102 and two gate arrays 104 and 106. Gate array 106 also performs some of the functions of the self-test initialization generator of FIG. 1.

Gate array 106 monitors temperature every 2 seconds in stand-by mode via a temperature sensor 131 while the MPU and other parts of the device are inactive. In the embodiment shown in FIG. 5, temperature sensor is a thermistor, such as model no. AL03006-535K-145-G1 from Keystone. If the current temperature read by sensor 131 is equal to or warmer than a HI temperature target or equal to or colder than a LO temperature target (stored in registers in gate array 106), gate array 106 "awakens" the rest of the device (i.e., changes the device from stand-by mode to self-test mode), and power is provided to MPU 102 and gate array 104. At that point, MPU 102 determines the reason it was awakened by reading an ONOFF_REASON register within gate array 106.

If the reason was the reaching of a temperature target, MPU 102 looks to its own more accurate temperature sensor, A/D temperature sensor 109 (such as an Analog Devices AD22100), to confirm the temperature. (While more accurate than sensor 131, sensor 109 requires more power than sensor 131 and is therefore only used when the device has been taken out of stand-by mode, as opposed to every 2 seconds as with sensor 131.) MPU 102 takes action appropriate to the new measured temperature, such as by looking to an RTHL stored in Flash ROM 114 to determine and indicate device battery status and by setting new temperature targets, as discussed above.

Any battery capacity test or other self-test called for by the method of this invention is run by MPU 102. Gate array 106 operates the device's visual status indicator 128 and beeper 119, which can function as an audible status indicator.

One consequence of using two different temperature sensors is the need for correlation between them. While the A/D temperature sensor 109 is sufficiently linear over the useful range of temperatures that might be encountered by the device, temperature sensor 131 is non-linear above 50° C. and below −10° C. A correction must be added to the sensor 131 temperature readings in the non-linear range to compensate for the non-linearity.

Modifications to the invention described above will be apparent to those skilled in the art. Such modifications are within the scope of this invention.

What is claimed is:

1. A method of indicating operational status of an electronic device, the method comprising the following steps:
    monitoring an environmental condition of the device;
    performing a plurality of self-tests at a plurality of monitored environmental conditions, to obtain self-test results;
    determining from results of the performing step whether the device operational status is acceptable or unacceptable at each monitored environmental condition;
    storing an association of self-test results and environmental conditions at which the self-tests were performed;
    indicating operational status of the electronic device for a partially monitored environmental condition based on the stored self-test results,
    wherein the plurality of self-tests comprise one or more different tests.

2. The method of claim 1 wherein the storing step comprises storing a maximum number of self-test results.

3. The method of claim 1 wherein the environmental condition is temperature.

4. The method of claim 3 wherein the device is a battery-operated device and the self-test is a battery capacity test.

5. The method of claim 4 further comprising:
    if a battery capacity test has not been performed within a target temperature, and if the target temperature is lower than a temperature of a lowest acceptable battery capacity test result and higher than a temperature of a highest unacceptable battery capacity test result; then
    performing a battery capacity test;
    storing an association of a battery capacity test result from the previous step s and the target temperature;
    indicating the device operational status from the results from the battery capacity test stored in the previous step, and
    setting a new target temperature.

6. The method of claim 5 further comprising:
    if a target temperature of an unacceptable battery capacity test result is higher than a target temperature of an unacceptable battery capacity test resul, then;
    performing a battery capacity test;
    storing an association of a result from the battery capacity test from the previous step and a current target temperature; and
    indicating an operational status of the device based on the result from the battery capacity test stored in the previous test.

7. The method of claim 4 wherein the battery-operated device is an external defibrillator.

8. A method of indicating operational status of an electronic device, the method comprising the following steps:
    monitoring an environmental condition of the device;
    performing a self-test at the monitored environmental condition;
    determining a self-test result from the self-test, the self-test result being a device operational status of acceptable or unacceptable; and
    storing an association of the self-test result and environmental condition at which the self-test was performed;
    repeating the above steps at a plurality of different monitored environmental conditions; and
    indicating operational status of the electronic device based on the stored self-test result at a presently monitored environmental condition.

9. The method of claim 8 wherein the storing step comprises storing a maximum number of self-tests results.

10. The method of claim 8 wherein the environmental condition is temperature.

11. The method of claim 10 wherein the device is a battery-operated device and the self-test is a battery capacity test.

12. The method of claim 11 further comprising:
    if a battery capacity test has not been performed within a target temperature, and if the target temperature is lower than a temperature of a lowest acceptable battery capacity test result and higher than a temperature of a highest unacceptable battery capacity test result; then
    performing a battery capacity test;
    storing an association of a battery capacity test result from the previous step and the target temperature;

indicating the device operational status from the results from the battery capacity test stored in the previous step; and setting a new target temperature.

13. The method of claim 12 further comprising:

if a target temperature of an unacceptable battery capacity test result is higher than a target temperature of an unacceptable battery capacity test result, then:

performing a battery capacity test;

storing an association of a result from the battery capacity test from the previous step and a current target temperature; and indicating an operational status of the device based on the result from the battery capacity test stored in the previous test.

14. The method of claim 11 wherein the battery-operated device is an external defibrillator.

* * * * *

UNITED STATES PATENT AND TRADEMARK OFFICE
CERTIFICATE OF CORRECTION

PATENT NO. : 5,944,741
DATED : August 31, 1999
INVENTOR(S) : Ochs et al.

It is certified that error appears in the above-identified patent and that said Letters Patent is hereby corrected as shown below:

On the title page item [57],

Line 20, delete "non-waning" and insert therefor --non-warning--.

Column 6, (line 49), delete "14" and insert therefor --14--.
Column 6, (line 50), delete "14" and insert therefor --14--.
Column 7, (line 28), delete "14" and insert therefor --14--.
Column 8, (line 39), delete "LO = 0 (disable)" and insert therefor --LO = Bin 0 (disabled) --.
Column 8, (line 47), delete "56 C." and insert therefor --50 C.--.
Column 8, (line 57), after "methods" insert --of this--.
Column 9, (line 9), delete "2" and insert therefor --2--.

Column 9, (line 56), after "conditions" delete ",".
Column 9, (line 64), delete "partially" and insert therefor --presently--.
Column 10, (line 16), delete "step s" and insert therefor --step--.
Column 10, (line 19), delete "step," and insert therefor --step;--.
Column 10, (line 25), delete "resul" and insert therefor --result--.

Signed and Sealed this

Thirtieth Day of January, 2001

Attest:

Q. TODD DICKINSON

*Attesting Officer*　　　　　*Director of Patents and Trademarks*